US010004894B2

(12) United States Patent
Bunch

(10) Patent No.: US 10,004,894 B2
(45) Date of Patent: Jun. 26, 2018

(54) DEFIBRILLATORS WITH MULTI-PAD ELECTRODES AND RELATED METHODS

(71) Applicant: Intermountain Intellectual Asset Management, LLC, Salt Lake City, UT (US)

(72) Inventor: Thomas Jared Bunch, South Jordan, UT (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 0 days. days.

(21) Appl. No.: 14/946,708

(22) Filed: Nov. 19, 2015

(65) Prior Publication Data

US 2016/0136415 A1 May 19, 2016

Related U.S. Application Data

(60) Provisional application No. 62/082,101, filed on Nov. 19, 2014, provisional application No. 62/146,163, filed on Apr. 10, 2015.

(51) Int. Cl.
*A61N 1/00* (2006.01)
*A61N 1/04* (2006.01)
*A61N 1/39* (2006.01)

(52) U.S. Cl.
CPC ........... *A61N 1/0492* (2013.01); *A61N 1/046* (2013.01); *A61N 1/39* (2013.01)

(58) Field of Classification Search
CPC .............................. A61N 1/0492; A61N 1/046
USPC .......................................................... 607/142
See application file for complete search history.

(56) References Cited

U.S. PATENT DOCUMENTS

| | | |
|---|---|---|
| 5,184,620 A | 2/1993 | Cudahy et al. |
| 5,466,244 A | 11/1995 | Morgan |
| 5,782,238 A | 7/1998 | Beitler |
| 5,951,598 A | 9/1999 | Bishay et al. |
| 6,178,357 B1 | 1/2001 | Gliner et al. |
| 6,272,385 B1 | 8/2001 | Bishay et al. |
| 6,400,975 B1 | 6/2002 | McFee |
| 6,532,379 B2 | 3/2003 | Stratbucker |
| 6,546,285 B1 * | 4/2003 | Owen ................ A61N 1/0452 607/142 |
| 6,560,473 B2 | 5/2003 | Dominguez |
| 6,575,914 B2 | 6/2003 | Rock et al. |
| 7,027,877 B2 | 4/2006 | Dupelle et al. |
| 7,245,974 B2 | 7/2007 | Dupelle et al. |
| 7,310,553 B2 | 12/2007 | Freeman |
| 7,486,990 B2 | 2/2009 | Sullivan |
| 7,590,456 B2 | 9/2009 | Craige et al. |
| 7,697,997 B2 | 4/2010 | Hyatt et al. |
| 8,180,457 B2 | 5/2012 | Matos |

\* cited by examiner

*Primary Examiner* — Nadia A Mahmood
(74) *Attorney, Agent, or Firm* — Stoel Rives LLP

(57) ABSTRACT

A defibrillator can include a first electrode and a second electrode where at least one of the electrodes includes more than one independently positionable pad. Such independently positionable pads, in various instances, may allow for alternative positioning of the components of an electrode when defibrillation is carried out during electrophysiological procedures in which placement of conventional electrodes is inadvisable, difficult, or impractical.

15 Claims, 11 Drawing Sheets

DEFIBRILLATORS WITH MULTI-PAD ELECTRODES AND RELATED METHODS

CROSS-REFERENCE TO RELATED APPLICATIONS

This application claims the benefit under 35 U.S.C. § 119(e) of U.S. Provisional Patent Application No. 62/082,101, titled DEFIBRILLATORS WITH MULTI-PAD ELECTRODES AND RELATED METHODS, filed on Nov. 19, 2014, and of U.S. Provisional Patent Application No. 62/146,163, titled DEFIBRILLATORS WITH MULTI-PAD ELECTRODES AND RELATED METHODS, filed on Apr. 10, 2015. The entire contents of each of the foregoing applications are hereby incorporated by reference herein.

TECHNICAL FIELD

This application generally relates to defibrillators and related methods. Some defibrillators suffer from one or more drawbacks or may perform less than optimally in one or more respects and/or contexts. Certain embodiments disclosed herein can address one or more of these issues.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
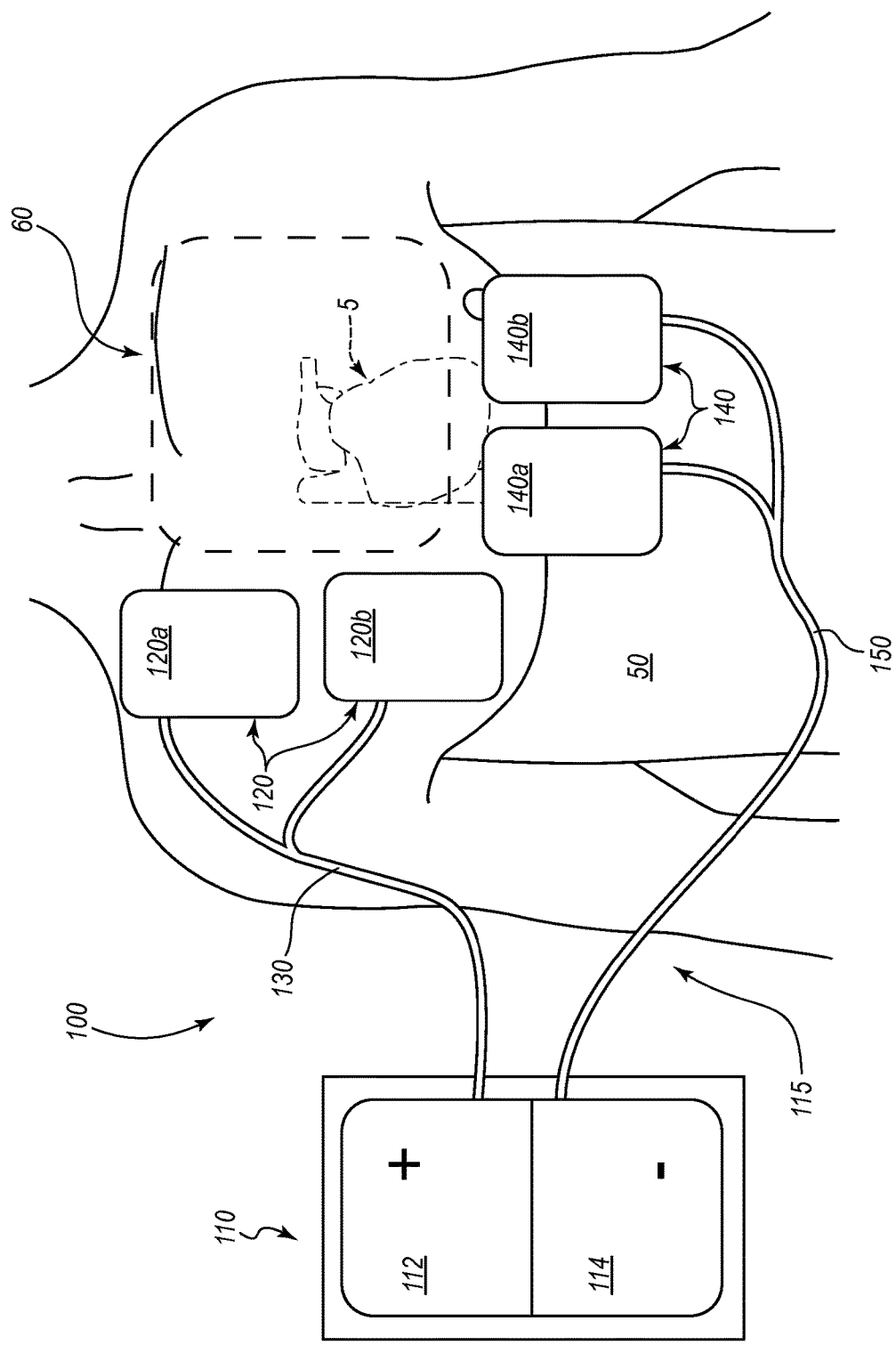
FIG. 1 is a front view of an embodiment of a defibrillator system that includes pads, which are depicted as having been arranged on a patient's chest to deliver an electrical pulse to a heart.

This application discloses various defibrillators and related methods. The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to" and "coupled to" are used in their ordinary sense, and are broad enough to refer to any suitable coupling or other form of interaction between two or more entities. Two components may be coupled to each other even though they are not in direct contact with each other. The phrases "attached to" or "attached directly to" refer to interaction between two or more entities which are in direct contact with each other and/or are separated from each other only by an adhesive, gel, and/or other medium or media that facilitate, enhance, or otherwise directly affect the attachment.

The term "conventional electrode," as used herein, refers to prior art electrodes. For example, conventional electrodes can include only one uninterrupted surface that is configured to contact the patient. Certain of such electrodes, which are sized for defibrillation, have a maximum length and maximum width such that the ratio between the maximum length and the maximum width is between 0.5 to 1 and 2 to 1.

Defibrillators are commonly used to alter the activity of a heart. For instance, a defibrillator may be used to deliver a therapeutic dose of electrical energy to a heart, or a portion thereof to treat cardiac dysrhythmias, ventricular fibrillation, or pulseless ventricular tachycardia. The electrical pulse delivered by the defibrillator may, in some circumstances, depolarize a critical mass of the heart, causing the heart to return to normal function.

Defibrillators generally include one or more capacitors that store electrical charge. The capacitor of the defibrillator may be configured to discharge upon actuation, causing electron movement in a direction from a first electrode (the anode) toward a second electrode (the cathode). Thus, by placing the first electrode on the patient at one side of a heart and a second electrode on the patient at a second (i.e., different) side of the heart and then discharging the capacitor(s), the defibrillator may deliver an electrical pulse to a heart.

Defibrillation can cause surface burns if adequate precautions are not taken. Surface burns can be alleviated or avoided by using a gel or adhesive that moistens the skin, thereby reducing the resistance between the electrodes and the skin. Additionally, surface burns can also be minimized by using electrodes with a relatively large surface, thereby distributing the pulse of electrical energy across a relatively large surface of patient's body. Electrodes are commonly about 100 millimeters by about 150 millimeters in size or larger.

In some circumstances, such as during some medical procedures in which defibrillators are commonly used, it may be difficult or impractical to place conventional electrodes at a suitable location on a patient's body due to one or more of the size of the electrodes or limited or restricted space available for placement of the electrodes. For instance, when placing an implantable cardioverter-defibrillator or a pacemaker, a significant portion of the patient's chest may be unavailable for placement of an electrode, as this portion of the chest may be within the sterile surgical preparation area. Locations for attaching conventional electrodes may be similarly limited during other medical procedures, such as ablations for atrial or ventricular arrhythmias, where imaging patches used as sensors are often attached to various locations on the patient's chest, midsection, and/or back. Locations where it is preferable to not contact the patient's skin with an electrode or a portion thereof are referred to herein as "restricted regions." Restricted regions can include, for example, portions of the skin within the surgical preparation area or regions to which other devices (e.g., imaging elements) are attached to the skin of a patient. Various embodiments disclosed herein may enable or otherwise facilitate the attachment of one or more electrodes to a patient where the space available for placement of electrodes is limited due to various restricted regions.

FIG. 1 provides a front view of an embodiment of a cardiac defibrillator 100 that includes a power supply 110 and an electrode assembly 115 coupled thereto. The electrode assembly 115 includes electrodes 120, 140 that are arranged on a patient's 50 chest to deliver an electrical pulse to the patient's 50 heart 5. The electrode 120 includes two electrode pads or patches 120a, 120b and an electrical lead 130 that couples the pads to a first terminal 112 of the power supply 110. The electrode 140 includes two electrode pads 140a, 140b and an electrical lead 150 that couples the pads to a second terminal 114 of the power supply 110.

In some embodiments, the first terminal 112 and second terminal 114 of the power supply 110 are components of a capacitor that is capable of storing electrical energy within the power supply 110. In some instances, the first terminal 112 may include a first plate of the capacitor, while the second terminal 114 includes a second plate of the capacitor that is separated from the first plate 112 by an insulator. In other embodiments, the first and second terminals 112, 114 may comprise multiple capacitors. Any other suitable arrangement for the first and second terminals is also contemplated. The power supply 110 desirably provides an electrical pulse or current for defibrillating the heart 5 of the patient that is delivered via the first and second terminals 112, 114. The electrode assembly 115 can desirably provide an electrical pathway for the pulse or current provided by the power supply 110.

The first electrode 120 may include a plurality of independently positionable pads 120a, 120b. For instance, a first pad 120a may be independently positionable relative to a second pad 120b. The pads 120a, 120b are independent of each other and are able to be moved and positioned separately relative to the patient, and the pads 120a, 120b may be arranged relative to the patient in a wide variety of different configurations. Each pad of the first plurality of independently positionable pads may be configured to directly attach to a patient's skin (e.g., via an adhesive and/or gel). The embodiment depicted in FIG. 1 shows an electrode 120 that has two independently positionable pads 120a, 120b. Other embodiments have electrodes that include 3, 4, 5, or 6 or more independently positionable pads.

The pads 120a, 120b depicted in FIG. 1 are coupled to the first terminal 112 via a first electrical lead 130. As depicted in FIG. 1, the first lead 130 includes an unbranched portion that extends from the first terminal 112 and a branched portion with separate branches that extend from the unbranched portion to each pad 120a, 120b of the first plurality of pads. Each of the pads 120a, 120b may be in electrical communication with the other of the pads 120b, 120a via the lead 130. In other embodiments, each pad 120a, 120b is coupled to the first terminal 112 via a separate lead 130 (such as in the manner depicted in FIG. 2A).

In the depicted embodiment, the second electrode 140 includes a second plurality of independently positionable pads 140a, 140b. These pads 140a, 140b are coupled to the second terminal 114 through lead 150 in a manner analogous to that described above in connection with the first plurality of independently positionable pads 120. In other embodiments, the second electrode 140 can include 3, 4, 5, or 6 or more pads. In still further embodiments, one of the electrodes 120, 140 can include a single pad (e.g., a standard defibrillator electrode) and the other of the electrodes 120, 140 can include multiple independently positionable pads (e.g., 2, 3, 4, 5, or 6 or more pads). Moreover, in some embodiments, each pad 140a, 140b is coupled to the second terminal 114 via a separate lead 150 (such as in the manner depicted in FIG. 2B).

In some embodiments, a plurality of independently positionable pads, such as the pads 120a, 120b and 140a, 140b (and/or additional pads) are connected in a daisy chain configuration. For example, rather than the leads 130, 150 being branched, the lead 130 can extend between the first terminal 112 and a first pad 120a, and a second lead (not shown) can extend from the first pad 120a to a second pad 120b. Signals can be communicated, for example, between the terminal 112 and the second pad 120b via the first lead 130 and the second lead. In other or further embodiments, the lead 150 can extend between the second terminal 114 and a first pad 140a, and a second lead (not shown) can extend from the first pad 140a to a second pad 140b. Signals can be communicated, for example, between the terminal 114 and the second pad 140 via the first lead 150 and the second lead. In embodiments having additional pads, additional leads can be used in like fashion to serially interconnect various pad portions of an electrode.

In some embodiments, the pads 120a, 120b, 140a, 140b may be smaller than conventional pads. In further or other embodiments, the pads 120a, 120b, 140a, 140b can be arranged in a fashion that avoids one or more restricted regions of a patient, such the restricted region 60 depicted in FIG. 1. This restricted region 60 is sized to approximate the surgical preparation area for various medical procedures, such as the surgical preparation area typically used when placing an implantable cardioverter-defibrillator or a pacemaker. Alternative restricted regions, such as the surgical preparation area for the subcutaneous placement of an implantable cardioverter-defibrillator may be larger than the restricted region 60 depicted in FIG. 1. As previously mentioned, in other or further instances, the restricted region 60 can be a region that is occupied by other devices attached to the skin of the patient.

An example of an arrangement of the independently positionable pads 120a, 120b, 140a, 140b of a first electrode 120 and second electrode 140 is provided in FIG. 1. In the depicted embodiment, the first pad 120a and the second pad 120b of the first plurality of pads are arranged such that the first pad 120a is disposed above the second pad 120b, with both pads attached over the right side of the patient's chest. The pads 140a, 140b of the second electrode 140 may be disposed on a different side of the patient's heart 5, such as below the patient's heart. The pads 140a, 140b may be arranged in a side-by-side arrangement. In this fashion, the electrodes 120, 140 may be placed on the patient 50 to avoid any restricted regions 60 and/or to supply a suitable electrical pulse to the heart 5. That is, in some arrangements, the pad or pads of the first electrode 120 and the pad or pads of the second electrode 140 can be positioned at an exterior of a restricted region in an orientation that provides an appropriate electrical path for providing a therapeutic pulse to the heart of a patient.

In the illustrative arrangement of the independently positionable pads 120a, 120b, 140a, 140b depicted in FIG. 1, the electrical energy from the power supply 110 (e.g., the energy stored by one or more capacitors) may be discharged, causing a current to pass between the electrodes 120, 140 and across the patient's heart 5 (or a portion thereof). Such electrical stimulation may alter the activity of the heart 5, such as restoring the heart 5 to its normal function. The plurality of pads 120a, 120b can reduce the current density of the electrical discharge, as compared with the discharge from similarly sized single pad, and thus may reduce injury to the patient.

In various embodiments, the electrode assembly 115 can be selectively coupled to and removed from the power source 110. Any suitable connection arrangement is possible, such as, for example, known port, plug, or socket arrangements. In other embodiments, the electrode assembly 115 may be permanently secured to the power source 110.

In some embodiments, each pad 120a, 120b, 140a, 140b can be a conventional electrode, such as any suitable known or commercially available electrode. For example, each of the pads 120a, 120b, 140a, 140b can be about 100 millimeters by about 150 millimeters in size or larger (e.g., being substantially rectangular in shape or having any other suitable configuration). The pads 120a, 120b can each have a separate lead 130 that is connected to the first terminal 112, and the pads 140a, 140b can each have a separate lead 150 that is connected to the second terminal 114. In various embodiments, the defibrillator 100 is configured to deliver up to about 300, 350, or 400 joules of electrical energy to a patient, or is configured to deliver energy to a patient within a range of, for example, from about 300 joules to about 400 joules or from about 350 joules to about 400 joules. Certain of such embodiments can be particularly well suited for use with obese patients, in which the delivery of a relatively large pulse can be desirable.

In certain of such embodiments, the power supply 110 can include a dedicated port for each lead 130, 150. Thus, for example, the power supply 110 can include four ports—two ports for two leads 130 and two further ports for two leads 150. In other embodiments, an adaptor may be used to connect multiple leads 130, 150 to a given port. For example, the power supply 110 may include a first port that is coupled with two leads 130 via an adaptor, and the power supply 110 may include a second port that is coupled with two leads 150 via an additional adaptor. Any suitable number of pads (e.g., 120a, 140a) and associated leads 130, 150 is contemplated.

As with other embodiments described herein, the power supply 110 can be configured to deliver the therapeutic energy in any suitable manner, such as by the actuation of a button. In certain of such embodiments, a single actuation of the power supply 110 can provide the full therapeutic dose of energy to the patient.

Figure 2A:
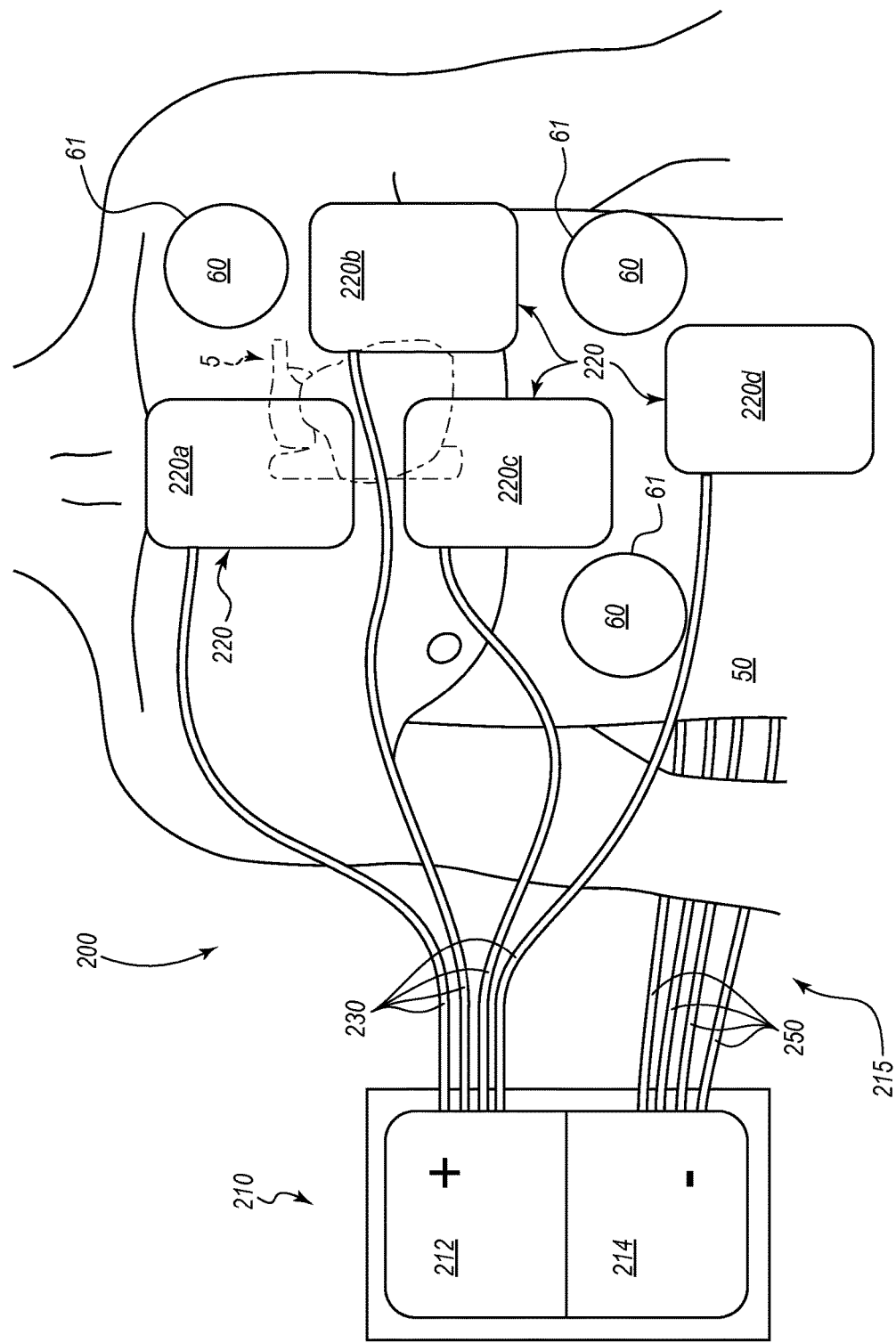
FIG. 2A is a front view of another embodiment of a defibrillator system that includes pads, which are depicted as having been arranged on the front and back of a patient.
Figure 2B:
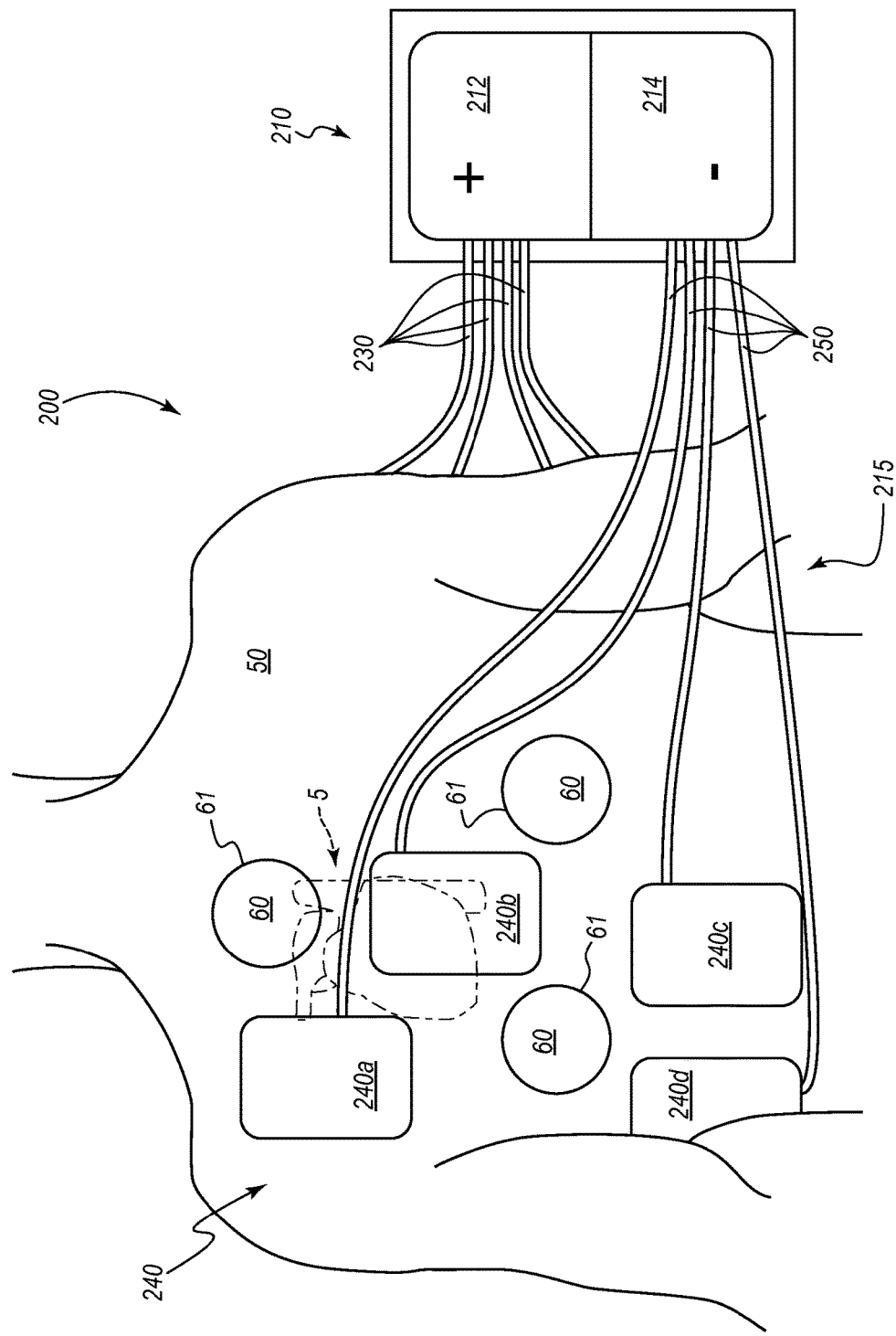
FIG. 2B is a rear view of the defibrillator of FIG. 2A with pads that are arranged on the front and back of the patient.

FIGS. 2A and 2B depict another embodiment of a defibrillator 200 that resembles the defibrillator 100 described above in certain respects. Accordingly, like features are designated with like reference numerals, with the leading digits incremented to "2." For example, the embodiment depicted in FIGS. 2 includes a power supply 210 and an electrode assembly 215 that may, in some respects, resemble the power supply 110 and electrode assembly 115 of FIG. 1. Relevant disclosure set forth above regarding similarly identified features thus may not be repeated hereafter. Moreover, specific features of defibrillators and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the defibrillator 200 and related components depicted in FIG. 2. Any suitable combination of the features, and variations of the same, described with respect to the defibrillator 100 and related components illustrated in FIG. 1, can be employed with the defibrillator 200 and related components of FIG. 2, and vice versa. This pattern of disclosure applies equally to further embodiments depicted in subsequent figures and described hereafter, wherein the leading digits may be further incremented.

FIGS. 2A and 2B depict alternative views of a defibrillator 200. More particularly, FIG. 2A provides a front view of the defibrillator 200, while FIG. 2B provides a back view of the defibrillator 200. The defibrillator 200 includes an electrical power supply 210 and an electrode assembly 215, which includes a first electrode 220, a second electrode 240, a plurality of first leads 230, and a plurality of second leads 250.

With reference to FIGS. 2A, the first electrode 220 includes four independently positionable pads 220a, 220b, 220c, 220d, each of which is coupled to a first terminal 212 of a power supply 210 via a separate lead 230. The leads 230 may place each pad of the first plurality of independently positionable pads in electrical communication with the other pads of the first plurality of independently positionable pads. Stated otherwise, in some embodiments, the pads 220a, 220b, 220c, 220d of the first electrode 220 may generally be at a common voltage. In the depicted embodiment, the first electrode 220 is placed on the front of the patient 50 (e.g., the chest). More particularly, the four independently positionable pads of the first electrode 220 are attached to the patient 50 in an arrangement that avoids three restricted regions 60 on the front of the patient. These restricted regions 60 are coextensive with, or are defined by, patches 61 (which are depicted schematically) that may be used to facilitate the imaging of one or more internal organs or regions. For example, such imaging patches 61 may be used in connection with mapping systems that guide a practitioner during ablation procedures for atrial or ventricular arrhythmias. In other or further embodiments, one or more of the restricted regions 60 can comprise a different type of device attached to the skin.

As depicted in FIG. 2B, the second electrode 240 includes four independently positionable pads 240a, 240b, 240c, 240d, each of which is coupled to a second terminal 214 of the power supply 210 via a separate lead 250. The leads 250 may place each pad of the first plurality of independently positionable pads in electrical communication with the other pads of the first plurality of independently positionable pads. Stated otherwise, in some embodiments, the pads 240a, 240b, 240c, 240d of the second electrode 240 may generally be at a common voltage. In the depicted embodiment, the second electrode 240 is generally placed on the back of the patient 50, with a portion of the pad 240d extending along a side of the patient 50. The four independently positionable pads of the second electrode 240 are attached to the patient 50 in an arrangement that avoids three restricted regions 60 on the back of the patient 50. Like the restricted regions 60 on the front the patient 50, the restricted regions 60 on the back of the patient 50 correspond with the size and location of patches 61 that may be used to facilitate imaging of one or more internal organs or regions.

When the cardiac defibrillator 200 is arranged as depicted in FIGS. 2A and 2B (i.e., with the first electrode 220 on the front of the patient 50 and the second electrode 240 on the back of the patient 50), the defibrillator 200 may be used to deliver a therapeutic pulse of electrical current to a heart 5, such as the human heart depicted in the drawings. It is to be understood that the multiple pads of the electrode 220 and the pads of the electrode 240 can be arranged in any suitable arrangement from avoiding one or more restricted regions 60 while being located in positions suitable for delivering a therapeutic electrical pulse to the heart.

Figure 3:
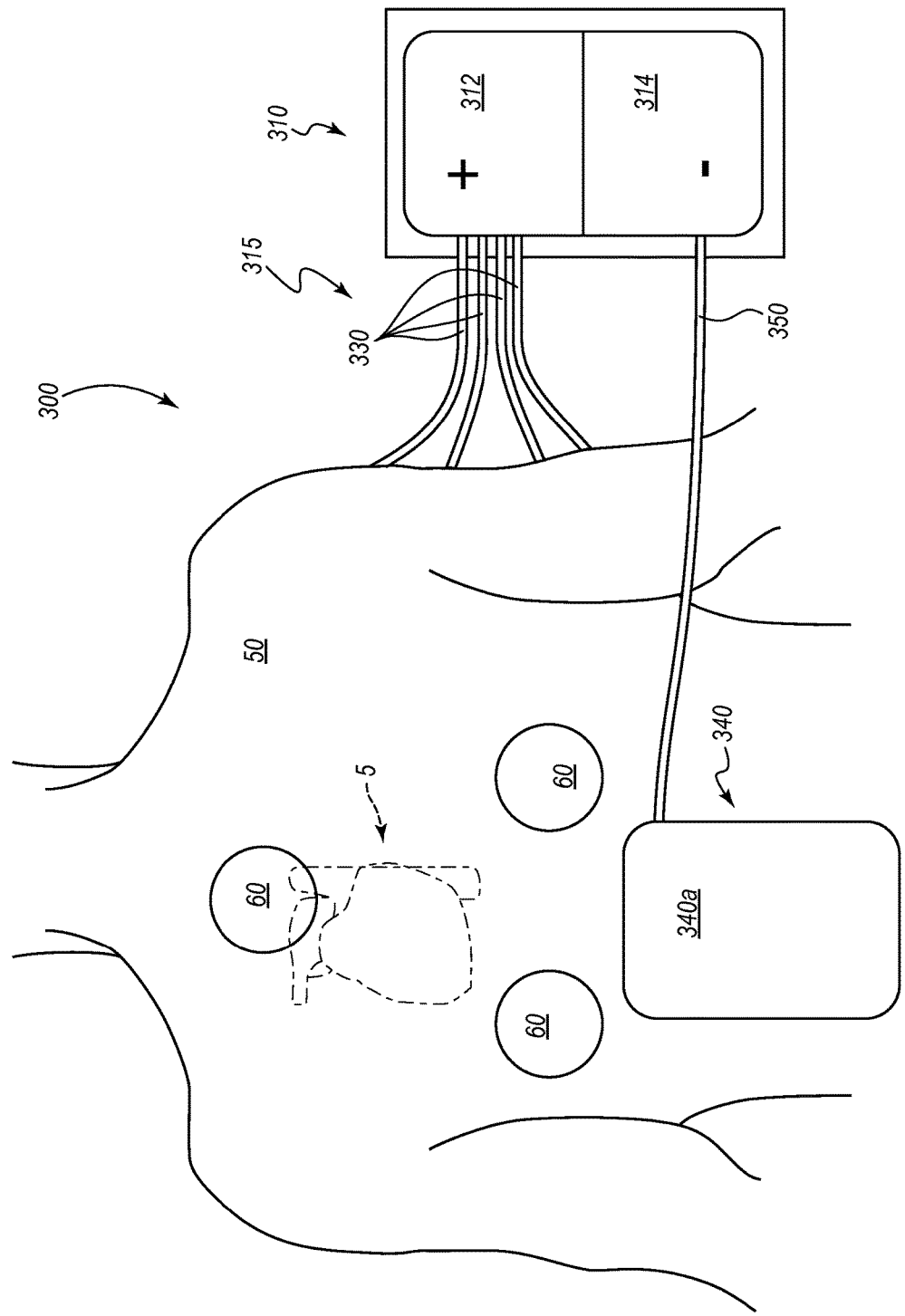
FIG. 3 is a rear view of another embodiment of a defibrillator system positioned on a patient.

FIG. 3 depicts another embodiment of a defibrillator 300, which includes a power supply 310 coupled with an electrode assembly 315. In this embodiment, a first terminal 312 of the power supply 310 is connected to an electrode (which is not shown, but which may resemble the electrode 220 discussed above) by a plurality of leads 330, while a second terminal 314 is connected to a second electrode 340 by a single lead 350. In this embodiment, the second electrode 340 has a single pad 340a. The pad 340a can have a single uninterrupted surface that is configured to contact the patient 50. As depicted in this embodiment, the second electrode 340 is disposed below the heart 5 and below the restricted regions 60 that are at the back of the patient 50. When the first electrode is attached to the patient as shown in FIG. 2A and the second electrode 340 is attached to the patient 50 as shown in FIG. 3, the discharge of stored energy in the power supply 310 causes an electrical current to pass between the electrodes and across at least a portion of the patient's heart 5, thereby delivering an electrical pulse to alter the activity of the heart 5.

Various methods may be used in connection with defibrillators, such as those described above. For instance, in some embodiments, a method for delivering an electrical pulse to alter the activity of a heart includes using a defibrillator having a first electrode and a second electrode to deliver an electrical pulse between the first electrode and the second electrode across at least a portion of a heart. The first electrode is coupled to a first terminal of a power supply through at least one or more first leads, the second electrode is coupled to a second terminal of the power supply through at least a second lead, and the first electrode includes a plurality of independently positionable pads.

In various methods, the first electrode and the second electrode may be positioned in a wide variety of suitable configurations. For instance, in some methods, a first electrode may be positioned such that each pad of the first plurality of independently positionable pads is disposed on a first side of a heart. In some methods, the second electrode may be positioned such that the second electrode is disposed on a second (i.e., different) side of the heart. In some methods, independently positionable pads of an electrode may be placed between two or more restricted regions (e.g., a surgical preparation area or an area occupied by a patch that is configured to facilitate imaging). In some methods the independently positionable pads are placed in regions between two or more restricted regions that are too small to accommodate the placement of a conventional electrode.

In some methods, independently positionable pads of either or both of the first electrode and the second electrode are placed on the chest of the patient. In some methods, the independently positionable pads of the first electrode are placed on the chest of patient and the independently positionable pads of the second electrode are placed on the back of the patient (e.g., between the scapula). Other locations for placement are also possible.

In view of the foregoing, in some embodiments, a defibrillator includes at least one electrode that has a plurality of individually positionable pads. The pads may be smaller than conventional electrode pads, and may be positioned between, adjacent to, or near restricted regions. The multiple pads can permit a user to select the size and shape of a region to which a therapeutic pulse is delivered.

In other or further embodiments, the multiple pads of an electrode may be shaped differently from conventional electrodes. In some embodiments, the pads have a shape specifically configured to readily fit between adjacent patches 61, such as those discussed above. For example, in some embodiments, the pads have an outer contour that is shaped complementarily to a patch 61 (e.g., a convex shape for receiving a rounded patch 61).

As previously discussed, in some embodiments, a defibrillator includes two electrodes that are respectively coupled with two terminals of a power supply. In some embodiments, one of the electrodes includes multiple electrode pads, whereas the other electrode includes a single electrode pad. In other embodiments, each electrode includes multiple electrode pads. The multiple electrode pads may be positioned as desired, such as at an exterior of restricted regions and in a position suitable for delivering a therapeutic pulse to a heart. In some embodiments, the multiple pads of a given electrode are coupled with a common electrical lead, whereas in other embodiments, at least some of the multiple pads of a given electrode are each coupled with separate electrical leads.

Figure 4:
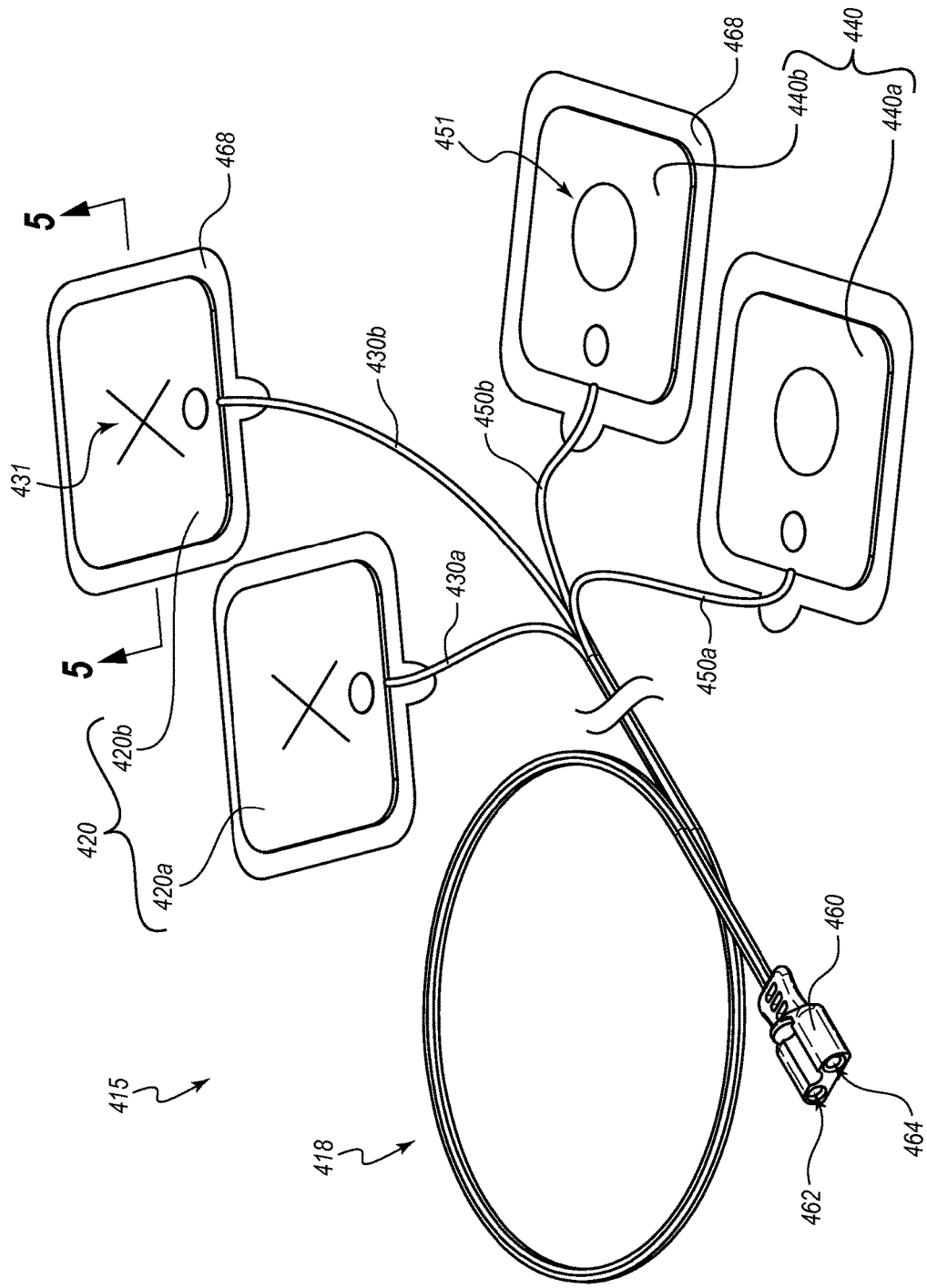
FIG. 4 is a perspective view of an embodiment of an electrode assembly.

FIG. 4 depicts an embodiment of an electrode assembly 415 that resembles the electrode assemblies 115, 215, 315 described above. The electrode assembly 415 includes a first electrode 420 and a second electrode 440. The first electrode 420 includes a plurality of electrode pads 420a, 420b that can be positioned on a patient independently of each other. As with other pads described herein, the pads 420a, 420b are moveable relative to each other and are physically separate from each other. Similarly, the second electrode 420 includes a plurality of electrode pads 440a, 440b that are physically separate from each other and are moveable relative to each other.

In the illustrated embodiment, each electrode pad 420a, 420b includes indicia 431 to indicate that these pads are associated with the first electrode 420. Similarly, each electrode pad 440a, 440b includes indicia 451 to indicate that these pads are associated with the second electrode 440. The indicia 431, 451 can thus assist the operator in determining appropriate placement for each pad due to the association of each pad with a particular terminal of a power supply.

In the illustrated embodiment, each electrode pad 420a, 420b, 440a, 440b includes a removable cover 468. As discussed further below, the covers 468 can be removed to expose an adhesive and/or gel that is configured to be placed against the skin of a patient during use of the electrode assembly 415.

The electrode assembly 415 includes a plurality of electrical leads 430a, 430b, 450a, 450b that are coupled with the electrode pads 420a, 420b, 440a, 440b, respectively. The electrical leads can include cables. In the illustrated embodiment, all of the electrical leads 430a, 430b, 450a, 450b are grouped together in a cable 418 at a proximal region thereof. The distal ends of the electrical leads are coupled with the electrode pads, and a distal region of each electrical lead 430a, 430b, 450a, 450b is able to move freely relative to the remaining leads to permit movement of the electrode pads relative to each other.

In the illustrated embodiment, a connector 460 is coupled to the cable 418. It may also be said that the connector 460 is coupled to each of the electrical leads 430a, 430b, 450a, 450b. In particular, a first electrical contact 462 of the connector 460 is coupled with the electrical leads 430a, 430b and a second electrical contact 464 of the connector 460 is coupled with the electrical leads 450a, 450b. The first electrical contact 462 can be configured to interface with a first terminal of a power supply, such as any of the power supplies 110, 210, 310 discussed above. The second electrical contact 464 can be configured to interface with a second terminal of a power supply (such as those discussed above). Any suitable arrangement is contemplated for establishing an electrical connection between the electrical contacts 462, 464 and the terminals of the power supply when the connector 460 is coupled with the power supply. For example, in the illustrated embodiment, the electrical contacts 462, 464 define electrical sockets that are configured to receive electrical pins or prongs of the first and second terminals. In other embodiments, one or more of the pin/socket arrangements can be reversed. Other suitable electrical contact mechanisms are also contemplated. In use, the electrical contact 462 can be at one of a positive or negative polarity at the same time the electrical contact 464 is at the other of the positive or negative polarity.

In some embodiments, the connector 460 is configured for use with known power supplies. For example, an interfacing portion of the connector 460 may be configured identically to that of known connectors for defibrillators, and the electrode assembly 415 may thus be used with known power supplies.

The indicia 431, 451 are examples of visual indicators that can be used to distinguish one or more electrode pads that are associated with the electrical contact 462 from one or more electrode pads that are associated with the electrical contact 462. Any other suitable visual indicator is possible. For example, the indicia 431, 451 can include one or more letters, symbols, colors, patterns, diagrams, and/or other features that can be visually perceived by a user of the electrode assembly 415 to distinguish one electrode pad (or set of electrode pads) from another electrode pad (or set of electrode pads). In various embodiments, the indicia 431, 451 are applied to one or more of the electrode pads and/or the electrical leads associated with the electrode pads. For example, in some embodiments, the electrode pads 420a, 420b and their associated electrical leads 430a, 430b can include a first color, whereas the electrode pads 440a, 440b and their associated electrical leads 450a, 450b can include a second color that is distinguishable from the first color.

Figure 5:
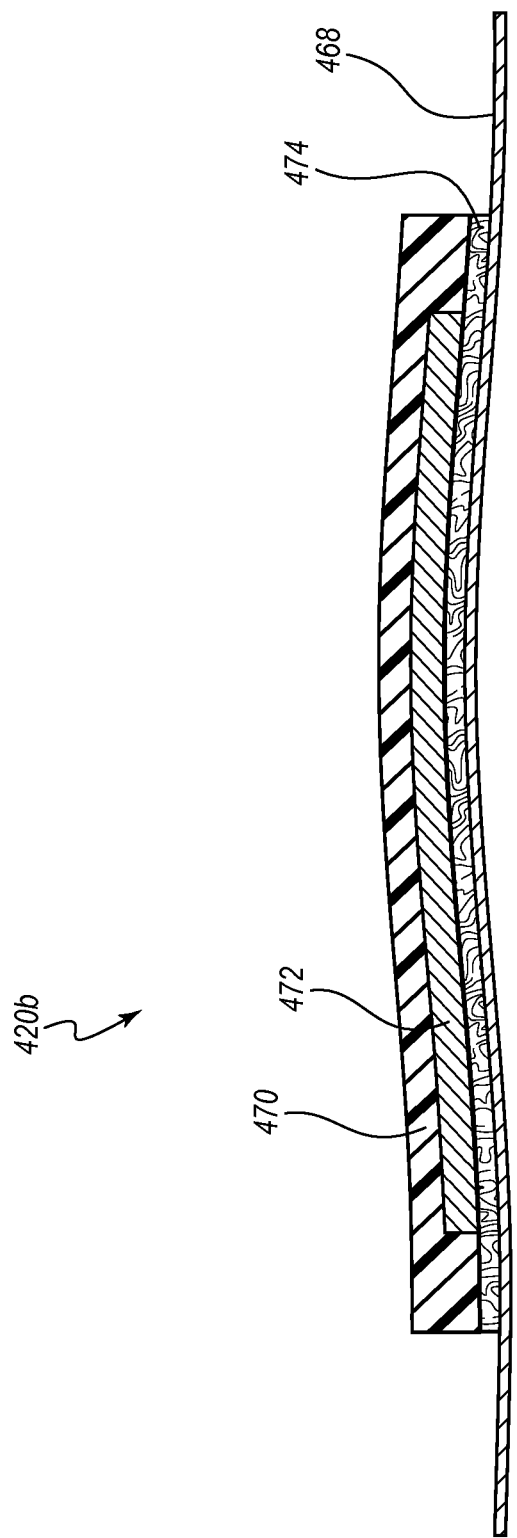
FIG. 5 is a cross-sectional view of an embodiment of an electrode pad taken along the view line 5-5 in FIG. 4.

FIG. 5 illustrates a cross-sectional view of the electrode pad 420b. The cross-sectional views of the electrode pads 420a, 440a, 440b of the illustrated embodiment would be similar to the view shown in FIG. 5. The electrode pad 420b includes a jacket or casing 470, which can include one or more layers of electrically insulating (e.g., dielectric) material. The electrode pad 420b can further include a conductive element 472, which may also be referred to as an electrode member, such as a metallic plate or any other suitable electrode device. A skin-contact layer 474 is also present, which can cover at least the conductive element 472 portion of the electrode pad 420b. The skin-contact layer 474 can include any suitable material, such as an adhesive for securing the electrode pad 420b to the skin of the patient and/or a gel for avoiding or inhibiting damage to the skin of the patient during defibrillation. (The adhesive and the gel may comprise the same material, in some instances.) The removable cover 468 can be secured to the skin-contact layer 474 and can be removed therefrom prior to placement of the electrode pad 420b on the skin of the patient.

With reference again to FIG. 4, as with other embodiments, described herein, the electrode assembly 415 can include any suitable number of electrode pads 420a, 440a. For example, in some embodiments, the electrode 420 can include a plurality of pads (e.g., two, three, four pads), whereas the electrode 440 can include a single pad. Differently sized and shaped pads are also contemplated.

Figure 6:
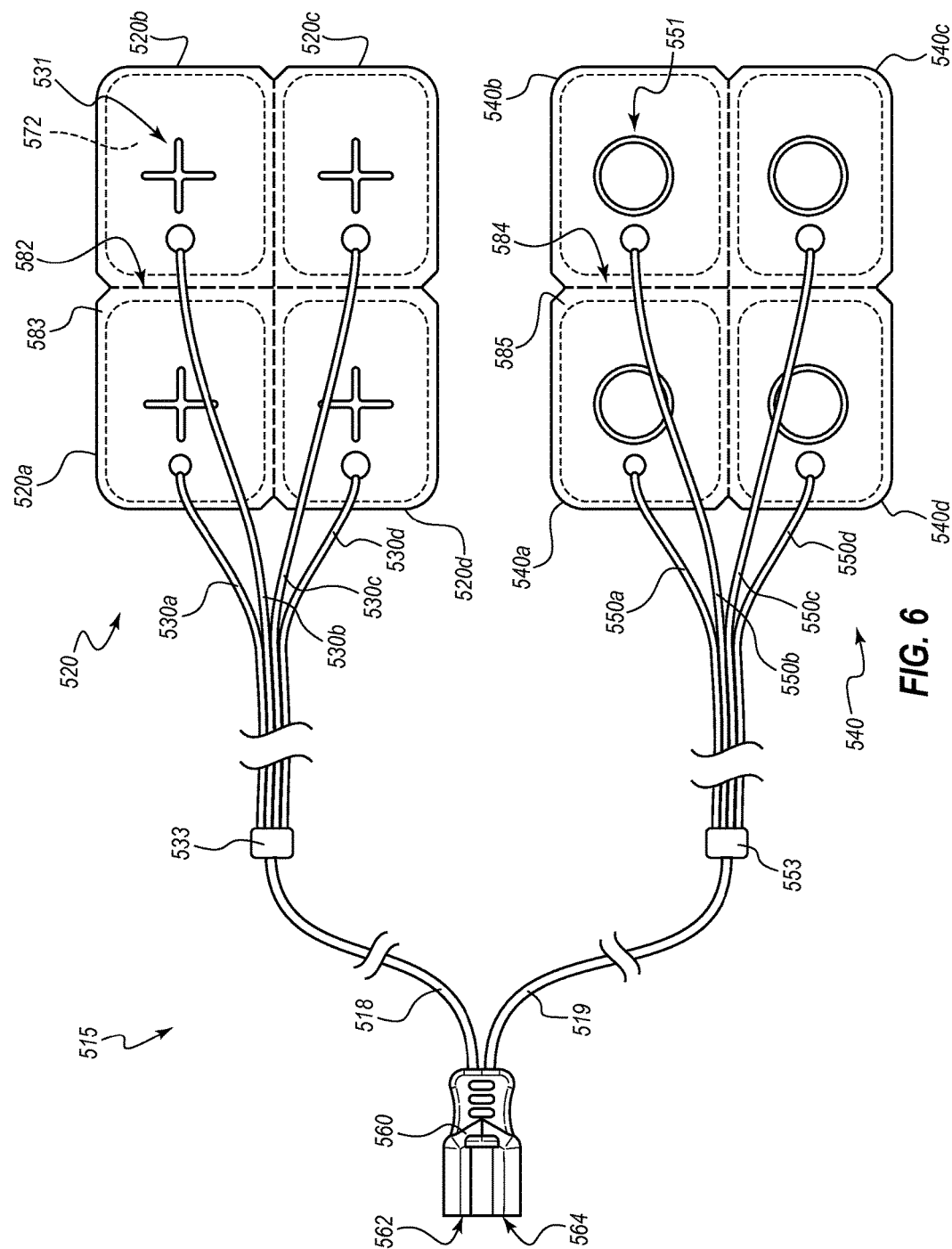
FIG. 6 is a plan view of another embodiment an electrode assembly that includes pads that are separable from each other.

FIG. 6 depicts another embodiment of an electrode assembly 515 that resembles the electrode assemblies 115, 215, 315, 415 described above in many respects. As with these other electrode assemblies, the electrode assembly 515 is compatible with various embodiments of defibrillator systems, such as the systems 100, 200 discussed above. The electrode assembly 515 includes a first electrode 520 and a second electrode 540.

In the illustrated embodiment, each of the first and second electrodes 520, 540 is formed as a unitary structure that includes a plurality of separable electrode pads. In particular, the illustrated electrode 520 includes four electrode pads 520a, 520b, 520c, 520d, and the electrode 540 includes four electrode pads 540a, 540b, 540c, 540d. Such an arrangement provides a practitioner with flexibility regarding the configuration of the electrodes 520, 540. In particular, the practitioner can selectively separate one or more of the electrode pads 520a, 520b, 520c, 520d or 540a, 540b, 540c, 540d from the remaining electrode pads as desired. The electrode pads can be situated relative to the body of the patient as desired, such as in manners discussed above.

In the illustrated embodiment, the electrode pads 520a, 520b, 520c, 520d are separated from adjacent pads via regions or lines of weakness 582. In the illustrated embodiment, the lines of weakness 582 are perforations in a layer 583 that is common to all of the electrode pads 520a, 520b, 520c, 520d. For example, the electrode 520 can include a polymeric layer or a layer of any other suitable material, and the perforations can extend through the layer 583 to permit ready separation of the electrode pads 520a, 520b, 520c, and/or 520d. Similarly, the electrode 540 can include a layer 585 that is common to all of the electrode pads 540a, 540b, 540c, 540d. The electrode 540 can further include regions or lines of weakness 584 positioned between adjacent electrode pads to permit separation of one or more of the electrode pads from the others. In other embodiments, the lines of weakness 582, 584 can comprise one or more of regions of reduced material thickness, serrations, frangible regions, or any other suitable configuration for permitting ready separation of the electrode pads from each other. The separation can be effected by tearing, pulling apart, or otherwise disrupting the line of weakness. In other embodiments, the electrode pads may be selectively separable and selectively attachable to each other. For example, the electrode pads may have fasteners (e.g., hook-and-pile fasteners, snaps, buttons, etc.) that permit the pads to be removed from or rejoined to adjacent electrode pads.

The electrode pads 520a, 520b, 520c, 520d can be positioned on a patient in a variety of configurations. For example, all of the pads may be used as a single unit, one of the pads may be separated from the other three, two pads may be separated from the other two, or all four pads may be separated from each other and used independently of each other. Similarly, the electrode pads 540a, 540b, 540c, 540d can be positioned on a patient in a variety of configurations. For example, all of the pads may be used as a single unit, one of the pads may be separated from the other three, two pads may be separated from the other two, or all four pads may be separated from each other and used independently of each other.

In the illustrated embodiment, each electrode pad 520a, 520b, 520c, 520d includes indicia 531 to indicate that these pads are associated with the first electrode 520, in manners such as discussed above. Similarly, each electrode pad 540a, 540b, 540c, 540d includes indicia 551 to indicate that these pads are associated with the second electrode 540. The indicia 531, 551 can thus assist the operator in determining appropriate placement for each pad due to the association of each pad with a particular terminal of a power supply. As discussed with respect to other embodiments, each electrode pad can include a conductive element 572, which are shown in phantom in FIG. 6.

The electrode assembly 515 includes a plurality of electrical leads 530a, 530b, 530c, 530d, 550a, 550b, 550c, 550d that are coupled with the electrode pads 520a, 520b, 520c, 520d, 540a, 540b, 540c, 540d respectively. The electrical leads can include cables. In the illustrated embodiment, all of the electrical leads 530a, 530b, 530c, 530d extend from a hub 533, at which point the electrical lead are grouped together within a cable 518 at a proximal region thereof. The distal ends of the electrical leads are coupled with the electrode pads, and a distal region of each electrical lead 530a, 530b, 530c, 530d is able to move freely relative to the remaining leads to permit movement of the electrode pads relative to each other. Similarly, all of the electrical leads 550a, 550b, 550c, 550d extend from a hub 553, at which point the electrical lead are grouped together within a cable 519 at a proximal region thereof. The distal ends of the electrical leads are coupled with the electrode pads, and a distal region of each electrical lead 550a, 550b, 550c, 550d is able to move freely relative to the remaining leads to permit movement of the electrode pads relative to each other In the illustrated embodiment, a connector 560 is coupled to the cables 518, 519. It may also be said that the connector 560 is coupled to each of the electrical leads 530a, 530b, 530c, 530d, 550a, 550b, 550c, 550d. In particular, a first electrical contact 562 of the connector 560 is coupled with the electrical leads 530a, 530b, 530c, 530d and a second electrical contact 564 of the connector 560 is coupled with the electrical leads 550a, 550b, 550c, 550d. The first electrical contact 562 can be configured to interface with a first terminal of a power supply, such as any of the power supplies 110, 210, 310 discussed above. The second electrical contact 564 can be configured to interface with a second terminal of a power supply (such as those discussed above). Any suitable arrangement is contemplated for establishing an electrical connection between the electrical contacts 562, 564 and the terminals of the power supply when the connector 560 is coupled with the power supply. For example, in the illustrated embodiment, the electrical contacts 562, 564 define electrical sockets that are configured to receive electrical pins or prongs of the first and second terminals. In other embodiments, one or more of the pin/socket arrangements can be reversed. Other suitable electrical contact mechanisms are also contemplated. In use, the electrical contact 562 can be at one of a positive or negative polarity at the same time the electrical contact 564 is at the other of the positive or negative polarity.

Figure 7A:
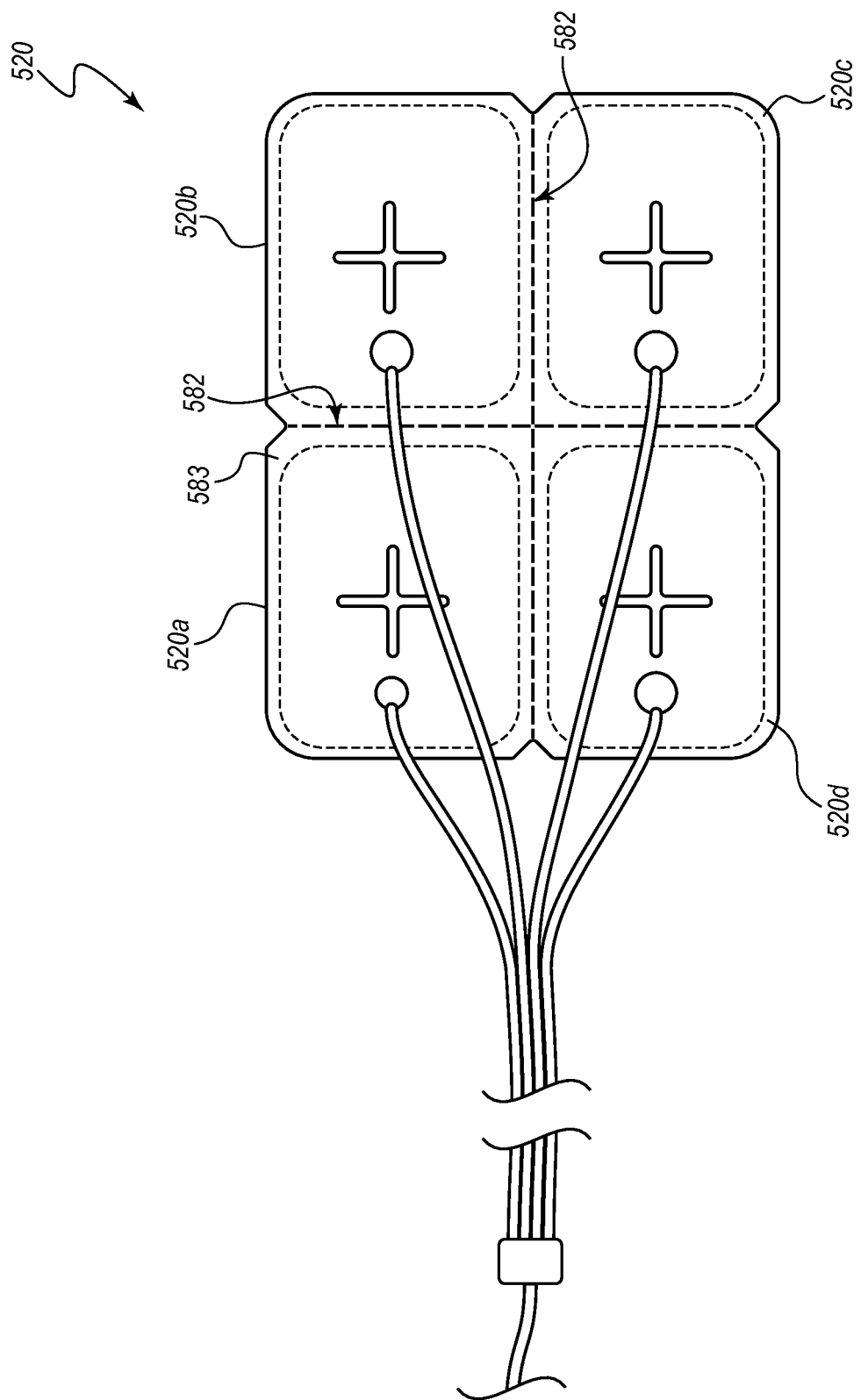
FIG. 7A is an enlarged view of a portion of the electrode assembly of FIG. 6, wherein separable portions of the electrode assembly are positioned together in a unitary pad.
Figure 7B:
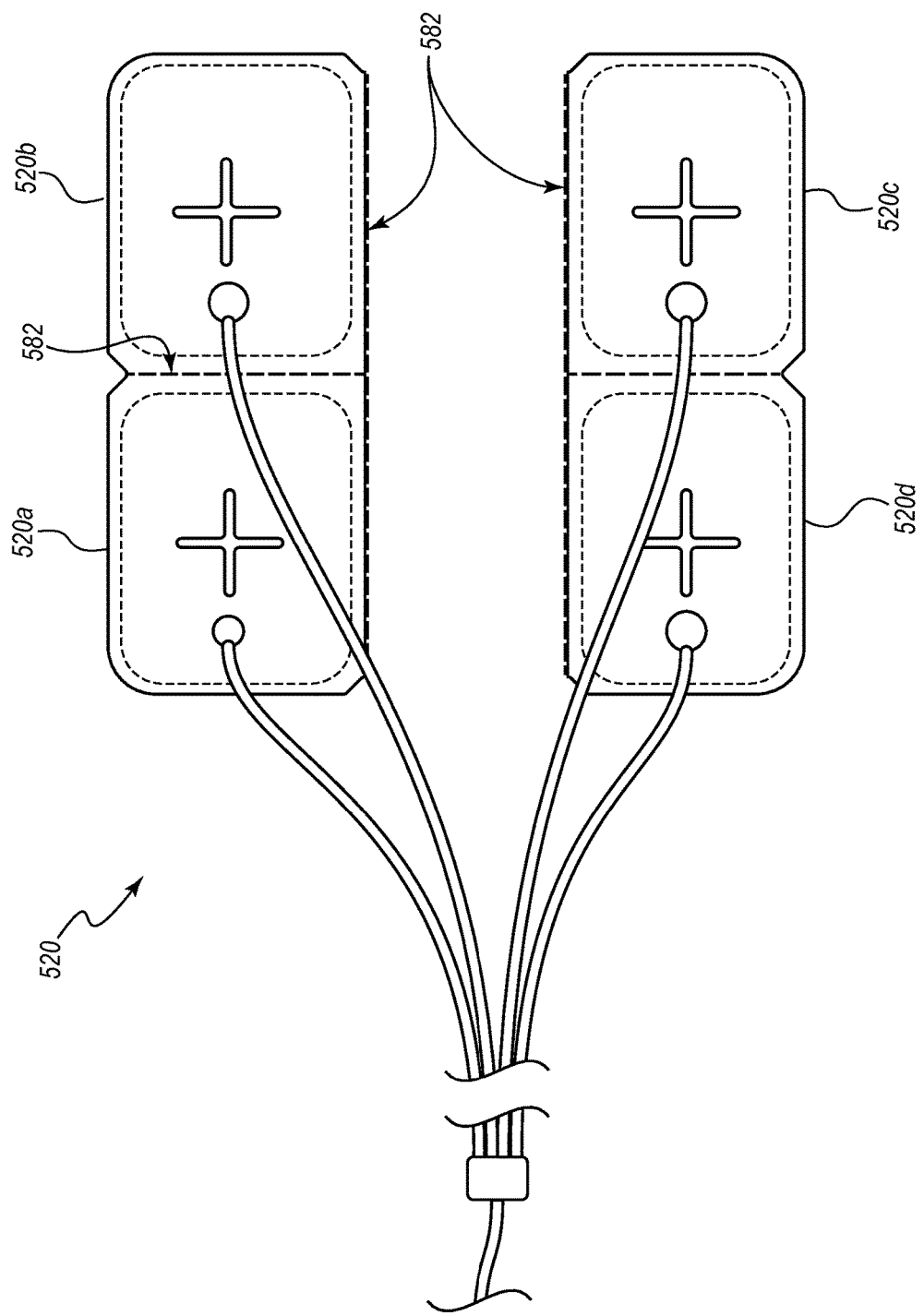
FIG. 7B is an enlarged view of the portion of the electrode assembly, such as depicted in FIG. 7A, wherein the unitary pad has been separated into two independent pads that are spaced from each other.
Figure 7C:
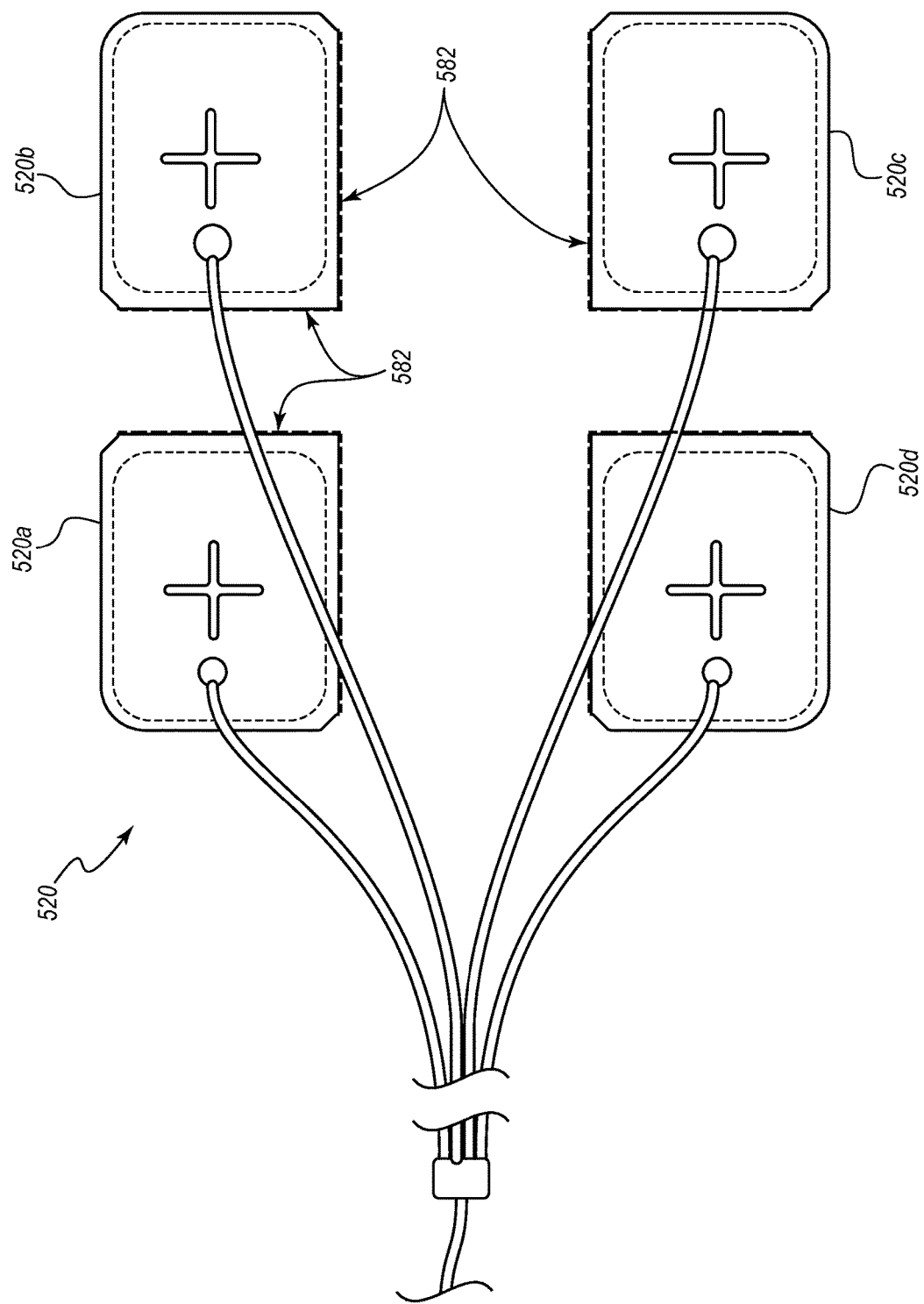
FIG. 7C is an enlarged view of the portion of the electrode assembly, such as depicted in FIG. 7A, wherein the unitary pad has been further separated into four independent pads that are each spaced from the other pads.

FIGS. 7A-7C depict a method whereby the electrode 520 can be separated into various configurations, or various pluralities of electrode pads. In FIG. 7A, the electrode 520 is shown in an initial state in which the common layer 583 is in a unified or monolithic state in which all of the electrode pads 520a, 520b, 520c, 520d are joined together. Two lines of weakness 582 are also shown, with one line being depicted in a vertical direction and the other in a horizontal direction. In FIG. 7B, the electrode 520 has been separated along the entirety of the horizontal line of weakness 582 to effectively create two separate electrode pads: one pad comprising the electrode pads 520a, 520b and the pad comprising the electrode pads 520c, 520d. In FIG. 7C, the electrode 520 has been further separated along the entirety of the vertical line of weakness 582, resulting in four separate electrode pads 520a, 520b, 520c, 520d. Other configurations are possible. For example, a single pad could be separated from the electrode 520 to yield a three-pad/single-pad arrangement by separating only a portion (e.g., one half) of each of the horizontal and vertical lines of weakness 582.

Figure 8:
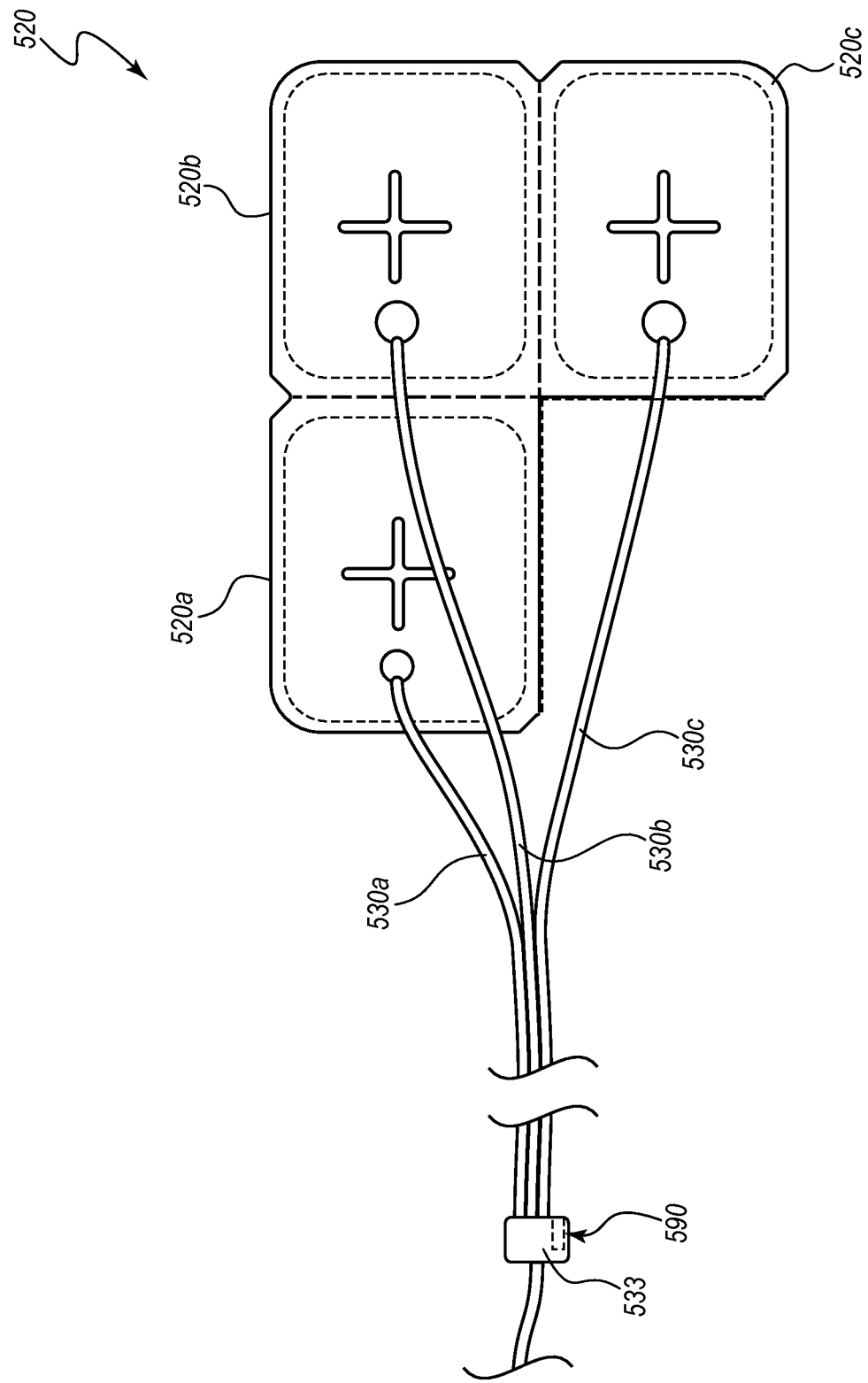
FIG. 8 is an enlarged view of a portion of another embodiment of an electrode assembly such as that depicted in FIG. 6, wherein the electrode includes four pads, and the electrode is depicted with one of the pads having been removed.

With reference to FIG. 8, in some embodiments, one or more of the electrode pads 520a, 520b, 520c, 520d or 540a, 540b, 540c, 540d of the respective first and second electrodes 520, 540 can be separated from the other pads of that electrode and additionally removed entirely from the electrode. For example, as depicted in FIG. 8, in some embodiments, one or more of the electrode pads 520a, 520b, 520c, 520d can be removed from the electrode 520, such as, for example, in circumstances where there is insufficient space on a patient to apply all of the pads 520a, 520b, 520c, 520d. In the illustrated embodiment, each of the pads 520a, 520b, 520c, 520d is removable from the hub 533. In the illustrated embodiment, the pad 520d has been removed from the hub 533. More particularly, a proximal end of the lead 530d to which the pad 520d is connected (see FIG. 6) is selectively coupled to the hub 533 via a releasable termination 590 (e.g., a socket or other connector configuration). The pad 520d is thus able to be disconnected from the hub 533 by disconnecting the lead 530d from the hub 533. In like fashion, one or more of the leads 530a, 530b, 530c can be removed from the hub 533, as needed or desired.

In other or further embodiments, one or more of the pads 520a, 520b, 520c, 520d can be releasably coupled to the distal ends of the electrical leads 530a, 530b, 530c, 530d, respectively. For example, the leads 530a, 530b, 530c, 530d may be permanently (or selectively) attached to the hub 533, and the distal ends of the leads 530a, 530b, 530c, 530d may be coupled with the pads 520a, 520b, 520c, 520d via releasable terminations 590. One or more of the pads 520a, 520b, 520c, 520d may thus be removed.

With reference again to FIG. 6, in some embodiments, some or all of the pads of a given electrode may be daisy chained in a manner such as described above. For example, in some embodiments, the lead 530a interconnects the hub 533 and the first pad 520a. In alternative embodiments, the hub 533 and/or the cable 518 can be omitted, and the lead 530a can interconnect the electrical contact 562 of the connector 560 and the first pad 520a. Similarly, the second lead 530b can interconnect the first pad 520a and the second pad 520b; the third lead 530c can interconnect the second pad 520b and the third pad 520c; and the fourth lead 530d can interconnect the third pad 520c and the fourth pad 520d. In some embodiments, one or more of the pads may be removable from the electrode 520 in a manner similar to that described in the previous paragraph. For example, the fourth pad 520d may be removed from the distal end of the daisy chain; or the fourth and third pads 520d, 520c may be removed from the distal end; etc.

With continued reference to FIG. 6, as with other embodiments described herein, the electrode assembly 515 can include any suitable number of electrode pads 520(a, b, c, d, etc.), 540(a, b, c, d, etc.). For example, in some embodiments, the electrode 520 can include a plurality of pads (e.g., two, three, four, five, six pads), whereas the electrode 540 can include a single pad. Differently sized and shaped pads are also contemplated. Embodiments of the electrode assemblies 115, 215, 315, 415, 515 described herein may further, or may instead, be used for monitoring a heartbeat of a patient.

As previously discussed, the electrode assemblies 115, 215, 315, 415, 515 can be configured for use in defibrillation, such that the assemblies 115, 215, 315, 415, 515 are capable of delivering a high amount of electrical energy to a patient in a manner suitable for altering heart activity. In various embodiments, the electrode assemblies 115, 215, 315, 415, 515 can be configured for delivering up to about 200, 250, 300, 350, or 400 joules of electrical energy to a patient, or can be configured to deliver energy to a patient, for example, within ranges of from about 200 to about 400 joules, from about 200 to about 300 joules, from about 150 to about 250 joules, from about 300 joules to about 400 joules, or from about 350 joules to about 400 joules.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure, that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A cardiac defibrillator comprising:
   an electrical power supply comprising a first terminal and a second terminal;
   a first electrode comprising a first plurality of independently positionable electrode pads coupled to the first terminal via one or more first leads; and
   a second electrode coupled to the second terminal via one or more second leads;
   wherein at least one of the first and second electrodes comprises a cathode and the other comprises an anode,
   wherein the cardiac defibrillator is configured to deliver a therapeutic pulse of electric current to a heart of a patient.

2. The cardiac defibrillator of claim 1, wherein each pad of the first plurality of independently positionable pads is in electrical communication with the other pads of the first plurality of independently positionable pads via the one or more first leads.

3. The cardiac defibrillator of claim 1, wherein each pad of the first plurality of independently positionable pads is configured to directly attach to the skin of the patient.

4. The cardiac defibrillator of claim 3, wherein each pad of the first plurality of independently positionable pads comprises an adhesive for directly attaching to the skin of the patient.

5. The cardiac defibrillator of claim 1, wherein the second electrode comprises a second plurality of independently positionable pads.

6. An electrode assembly comprising:
   a first electrode comprising:
      a first electrode pad comprising at least one of an adhesive or gel to secure the first electrode pad to the skin of a patient; and
      a second electrode pad comprising at least one of an adhesive or gel to secure the second electrode pad to the skin of a patient, the second electrode pad being configured to move independently relative to the first electrode pad to permit the first and second electrode pads to be independently positioned on a patient;
   a connector configured to be selectively coupled with a defibrillator power supply, the connector comprising first and second electrical contacts that are configured to be coupled with first and second terminals, respectively, of the defibrillator power supply, the first electrical contact being electrically coupled with each of the first and second electrode pads;
   a second electrode comprising:
      a third electrode pad electrically coupled with the second electrical contact of the connector; and
   visual indicia indicating the first and second electrode pads are associated with the first electrical contact and indicating the third electrode pad is associated with the second electrical contact,
   wherein at least one of the first and second electrodes comprises a cathode and the other comprises an anode.

7. The electrode assembly of claim 6, further comprising a fourth electrode pad electrically coupled with the second electrical contact of the connector, wherein the third and the fourth electrode pads are configured to move independently of each other so as to be independently positioned on a patient.

8. The electrode assembly of claim 7, wherein the third and fourth electrode pads are integrally joined to each other via a common layer, and wherein the common layer comprises a region of weakness that can be disrupted to effect separation of the third and fourth electrode pads.

9. The electrode assembly of claim 6, wherein the first and the second electrode pads are electrically coupled with the first electrical contact via separate electrical leads.

10. The electrode assembly of claim 9, wherein at least a portion of the visual indicia is present on the electrical leads.

11. The electrode assembly of claim 6, wherein the first, second, and third electrode pads include at least a portion of the visual indicia.

12. The electrode assembly of claim 6, wherein the first and second electrode pads are integrally joined to each other via a common layer, and wherein the common layer comprises a region of weakness that can be disrupted to effect separation of the first and second electrode pads.

13. The electrode assembly of claim 6, wherein the first and second electrode pads are selectively detachable from each other.

14. An electrode assembly comprising:
   a first electrode comprising:
      a first electrode pad comprising a first conductive element and at least one of an adhesive or gel to secure the first electrode pad to the skin of a patient;
      a second electrode pad comprising a second conductive element that is separate from the first conductive element and comprising at least one of an adhesive or gel to secure the second electrode pad to the skin of a patient,
      a layer of material that defines at least a portion of each of the first and second electrode pads, wherein the layer of material comprises a region of weakness that can be disrupted to effect separation of the first electrode pad from the second electrode pad to permit the first and second electrode pads to be independently positioned on a patient;
   a connector configured to be selectively coupled with a defibrillator power supply, the connector comprising first and second electrical contacts that are configured to be coupled with first and second terminals, respectively, of the defibrillator power supply, the first electrical contact being electrically coupled with each of the first and second electrode pads; and
   a second electrode comprising:
      a third electrode pad electrically coupled with the second electrical contact of the connector,
   wherein at least one of the first and second electrodes comprises a cathode and the other comprises an anode.

15. The electrode assembly of claim 14, wherein the first electrode pad is configured to be removable from the electrode assembly so as to be electrically decoupled from the first electrical contact of the connector.

* * * * *